US008715651B2

(12) United States Patent
Maestro et al.

(10) Patent No.: US 8,715,651 B2
(45) Date of Patent: May 6, 2014

(54) **USE OF AT LEAST ONE EXTRACT OF FLOWERS OF *CAMELLIA JAPONICA* ALBA PLENA FOR MOISTURIZING THE SKIN**

(75) Inventors: Yannick Maestro, Martigues (FR); Christelle Lasserre, Jersey City, NJ (US)

(73) Assignee: Chanel Parfums Beaute, Neuilly sur Seine (FR)

( * ) Notice: Subject to any disclaimer, the term of this patent is extended or adjusted under 35 U.S.C. 154(b) by 1 day.

(21) Appl. No.: 13/521,091

(22) PCT Filed: Jan. 4, 2011

(86) PCT No.: PCT/EP2011/050053
§ 371 (c)(1),
(2), (4) Date: Jul. 9, 2012

(87) PCT Pub. No.: WO2011/083110
PCT Pub. Date: Jul. 14, 2011

(65) Prior Publication Data
US 2012/0282244 A1 Nov. 8, 2012

Related U.S. Application Data

(60) Provisional application No. 61/293,312, filed on Jan. 8, 2010.

(51) Int. Cl.
*A61K 8/97* (2006.01)

(52) U.S. Cl.
USPC .......................................... 424/115; 424/729

(58) Field of Classification Search
CPC ................ A61K 2300/00; A61K 31/728
USPC ............................................ 424/115, 729
See application file for complete search history.

(56) References Cited

U.S. PATENT DOCUMENTS

| 2002/0054927 | A1 | 5/2002 | Paufique |
| 2004/0142335 | A1 | 7/2004 | Petersohn et al. |
| 2009/0215881 | A1 | 8/2009 | Delaire et al. |

FOREIGN PATENT DOCUMENTS

| FR | 2787996 A1 | 7/2000 |
| FR | 2813525 A1 | 3/2002 |
| FR | 2905858 A1 | 3/2008 |
| JP | 2008137998 A * | 6/2008 |
| KR | 10-2003-0090574 * | 10/2003 |
| KR | 20070000714 A | 1/2007 |
| KR | 20090075281 A | 7/2009 |
| KR | 20090107128 A | 10/2009 |
| WO | 2006134282 A1 | 12/2006 |
| WO | 2009010356 A1 | 1/2009 |

OTHER PUBLICATIONS

Onodera et al., Bioscience, Biotechnology, and Biochemistry, vol. 70, No. 8, p. 1995-1998, 2006.*

Onodera et al., Bioscience, Biotechnology and Biochemistry, vol. 70, No. 8, p. 1995-1998, 2006.*
Bhatt et al: "Not all *Camellias* are created equal: The effect of *Camellia japonica* extracts on barrier function and protection from environmental insult", Journal of Investigative Dermatology, Nature Publishing Group, 2011, vol. 131, No. Suppl.1, p. S53, XP009162544.
Database WPI, Week 200757, Thomson Scientific, London, GB, AN 2007-596357, 2007, XP002683019, & KR 2007 0000714 A (Bioland Ltd).
Database WPI, Week 200978, Thomson Scientific, London, GB, AN 2009-Q31877, 2009, XP002683020, & KR 2009 0107128 A (Skincure Inc).
Database WPI, Week 200962, Thomson Scientific, London, GB, AN 2009-L95638, 2009, XP002683021, & KR 2009 0075281 A (JSLAB).
Database GNPD [Online], Mintel, 2009, Uni-President Pharmaceuticals: "My Beauty Diary *Camellia* Mask", XP002683022, Database accession No. 1032205.
*Camellia japonica* Flower Extract and *Camellia japonica* Flower Water, in: T E Gottschalck, G N McEwen Jr., International Cosmetic Ingredient Dictionary and Handbook, 11th ed., 2006, The Cosmetics, Toiletries and Fragrance Association, Inc., Washington, DC CD, XP002683023.
Boxman et al., "Induction of HSP27 nuclear immunoreactivity during stress is moudulated by vitamin C", Experimental Dermatology, 2002, vol. 11. pp. 509-517.
Clark et al., "Involvement of the Heme Oxygenase-Carbon Monoxide Pathway in Keratinocyte Proliferation", Biochemical and Biophysical Research Communications, 1997, vol. 241, pp. 215-220.
Hanselmann et al., "Haem oxigenase-1: a novel player in cutaneous wound repair and psoriasis?", Biochem. J., 2001, vol. 353, pp. 459-466.
Jonak et al., "The expression of the 27-kd heat shock protein in keratinization disorders: an immunohistological study", Human Pathology, 2005, vol. 36, pp. 686-693.
O'Shaughnessy et al., "AKT-dependent HspB1 (Hsp27) Activity in Epidermal Differentiation", The Journal of Biological Chemistry, 2007, vol. 282, No. 23, pp. 17297-17305.
Pfaffl, Michael, "A new mathematical model for relative quantification in real-time RT-PCR", Nucleic Acids Research, 2001, vol. 29, No. 9 00, pp. 2002-2007.
International Search Report dated Dec. 12, 2012, from corresponding PCT application.

* cited by examiner

*Primary Examiner* — Susan Hanley
*Assistant Examiner* — Damon B Bowe
(74) *Attorney, Agent, or Firm* — Young & Thompson

(57) ABSTRACT

The present invention relates to a cosmetic composition containing an extract of flowers of Camellia Japonica Alba Plena, as well as the cosmetic use thereof, for moisturizing and/or protecting human skin against drying. It also relates to an extract of flowers of Camellia Japonica Alba Plena, characterized in that it can be obtained by extraction of flowers by at least one alcoholic solvent.

13 Claims, No Drawings

USE OF AT LEAST ONE EXTRACT OF FLOWERS OF *CAMELLIA JAPONICA* ALBA PLENA FOR MOISTURIZING THE SKIN

The present invention relates to a cosmetic composition containing an extract of flowers of Camellia Japonica Alba Plena, as well as the cosmetic use thereof, for moisturizing and/or protecting human skin against drying. It also relates to an extract of flowers of Camellia Japonica Alba Plena, characterized in that it can be obtained by extraction of the flowers by means of at least one alcoholic solvent.

The skin is made up of three main layers, namely, starting from the surface: the epidermis, the dermis and the hypodermis.

The epidermis is in particular constituted of keratinocytes (primarily), melanocytes (involved in skin pigmentation) and Langerhans cells. Its function is to protect the body from the environment and to ensure its integrity, and notably to block the penetration of microorganisms or chemical substances, and to prevent evaporation of the water contained in the skin.

For performing this function, the keratinocytes undergo a continuous process of directed maturation during which the keratinocytes located in the basal layer of the epidermis form, in the terminal step of their differentiation, corneocytes which are fully keratinized dead cells in the form of cornified envelopes constituted of proteins and lipids such as ceramides. During this differentiation process, intercorneocytic epidermal lipids are also formed and then organized in the form of bilayers (sheets) in the stratum corneum. They participate, with the aforementioned cornified envelopes, in the barrier function of the epidermis.

The barrier function of the epidermis may, however, be disturbed in certain climatic conditions (under the action of cold and/or wind, for example), or notably as a result of stress or fatigue, thus promoting the penetration of allergens, of irritants or of microorganisms, which thus cause drying of the skin, and this may produce sensations of discomfort such as tightness or redness, as well as affecting the radiance and suppleness of the skin.

For preventing or correcting this phenomenon, the application of cosmetic compositions containing hygroscopic agents, such as sugars or polyols, on the skin, with the intention of trapping the water present in the skin and thus impeding its evaporation, is known. There is also the conventional use of fats, for forming an occlusive film on the skin, which helps to impede the evaporation of water. Moreover, these compositions frequently incorporate active substances that act on one or more of the various biological targets involved either in the processes of regeneration of the skin, in particular in the differentiation of keratinocytes, the synthesis of epidermal lipids and the cohesion of corneocytes, or in the endogenous synthesis of constituents of the Natural Moisturizing Factor (NMF) of the skin, in particular in the synthesis of proteoglycans.

Examples of these active substances are notably the α- and β-hydroxy acids, notably lactic acid, glycolic acid and salicylic acid; urea; or aminosulfonic compounds.

However, there is still a need for new cosmetic active substances that are more effective in counteracting drying of the skin.

Moreover, bearing in mind consumers' ever increasing demand for natural products containing as few synthetic ingredients as possible, and the increasingly strict regulations that have to be met by compounds from the chemical industry, it would be desirable for these cosmetic active ingredients to be of vegetable origin.

Now, the applicant has been able to show that drying of the skin can be counteracted effectively using a botanical extract, namely an extract of flowers of Camellia Japonica Alba Plena.

In fact, the applicant has demonstrated that an extract of flowers of Camellia Japonica Alba Plena, which to the best of their knowledge has never been used before in cosmetics, is capable, after topical application on the skin, of stimulating the biomarkers HSP27, HSP32 and PPAR-β/δ simultaneously.

The heat-shock proteins (HSP), also called stress proteins, were discovered gradually, following exposition of the HSP principle by the researcher Ritossa in 1962. They are very ancient biological tools, which have been conserved during the evolution of species.

The HSPs are large molecules of the polypeptide type, with long chains and complex structures. There are HSPs of various masses (they are grouped according to their molecular weight, for example HSP 27 (27 kDa), HSP 70 (70 kDa), etc.), and with various spatial conformations, which determine and influence the activity of the protein. Their role is demonstrated in the differentiation of certain types of cells, in combating infections and chemical or toxic stresses, as well as protection against hypoxia. The HSPs are so-called "chaperone" proteins which protect other proteins against thermal denaturation and aggregation. The stress proteins can thus suppress harmful radicals and in particular make it possible to maintain cellular functions and restore metabolic functions to basic values. The role of the HSPs is therefore maintenance of protein homeostasis, in order to preserve cellular integrity against denaturing agents.

The proteins HSP 27 and HSP 32 are expressed in the stratum corneum of the human epidermis.

It was observed that the level of expression of HSP27 was increased as a result of various stress phenomena as well as during differentiation or cellular proliferation. HSP 27 serves as a biomarker notably during irritation of the skin (Boxman ll. et al. 2002, *Exp Dermatol*, 11(6): 50917). It was shown recently that HSP 27 is involved in the process of keratinization of the stratum corneum and the maturation of filaggrin (O'Shaughnessy et al. *J Biol Chem*, 2007, 282: 17297-305). Moreover, a decrease in expression of the mRNA coding for HSP 27 was observed during skin aging (US 2004/0142335).

HSP-32 is also known as heme oxygenase-1. Heme oxygenase serves for degradation of heme, a promoter of the peroxidation of lipids and of the formation of free radicals. HSP 32 was observed to play an important role in tissue repair and in the differentiation of keratinocytes (Hanselmann et al. 2001, *Biochem J.*, 353, 459-466; Clark et al., *Biochem. Biophys. Res. Commun.*, 241, 215-220). HSP 32 is a biomarker that is much used for its essential antioxidant function, for detecting the effects of certain molecules involved in protecting the skin against the harmful effects (oxidation) of UV radiation (FR 2787996, FR2813525).

The PPARs (peroxisome proliferator-activated receptors) are members of the superfamily of nuclear receptors. They participate in many metabolic and cellular processes. Currently, three isoforms of the PPARs have been identified in numerous vertebrates, and their differential tissue distribution reflects specific functions: PPAR-α (also called NR1C1), PPAR-β/δ (or NR1C2) and PPAR-γ (NR1C3). Through its role as regulator of lipid metabolism, proliferation and differentiation of keratinocytes, PPAR-β/δ is known to regulate skin permeability (Calleja et al., 2006, *Genes Dev* 20, 1525-1538).

The present invention thus relates to a cosmetic composition containing, in a physiologically acceptable medium, at least one extract of flowers of Camellia Japonica Alba Plena.

The present invention also relates to the cosmetic use of this composition for moisturizing and/or protecting human skin against drying.

The present invention also relates to an extract of flowers of Camellia Japonica Alba Plena characterized in that this extract can be obtained by extraction of flowers by means of at least one alcoholic solvent.

The Camellia is a genus of flowering plants of the family Theaceae, originating from east and south-east Asia from the Himalayas as far as Japan and Indonesia. In Japan and China, Camellia flowers are recognized for their antibacterial, antioxidant, hemostatic, antiinflammatory/soothing, astringent, gastro-protective and tonic properties. Mixed with sesame oil, they have been used as unguents in the treatment of burns and in the treatment of internal and external hemorrhages and inflammation. Botanists give different numbers of species in the genus, varying between 100 and 250 species. Among these species, the applicant was quite particularly interested in *Camellia japonica*, which itself contains a lot of different varieties, such as Dr Tinsley, Broceliande or Fire Falls. This invention specifically pertains to the variety Camellia Japonica Alba Plena, which demonstrated a higher stimulation of the expression of PPAR β/δ and HSP-27 than other varieties of the same species. This plant extract is harvested in the South-West of France.

The extract of flowers of Camellia Japonica Alba Plena usable in the present invention can be obtained by alcoholic extraction by means of at least one monohydric alcohol such as ethanol, methanol or isopropanol and/or of at least one glycol such as propylene glycol or dipropylene glycol, optionally mixed with water. Extraction is performed in the absence of any solvent other than water and alcohols. The solvent used according to the invention is preferably ethanol, for example at 96% (volume/volume).

Generally, extraction can be performed on fresh or dried flowers, optionally ground. Extraction is generally performed by immersing or by gently agitating the flowers in one or more of the aforementioned solvents at temperatures in the range, for example, from room temperature to 100° C., and advantageously from 30 to 70° C., for a time from about 30 min to 12 h and preferably from 1 to 8 hours. The solution is then preferably filtered to remove the insoluble substances of the plant. If applicable, the solvent is also removed, if it is a volatile solvent such as, for example, ethanol, methanol or isopropanol.

The solvent/substance ratio (in volume/weight) can for example be between 1:1 and 100:1 and preferably between 3:1 and 30:1.

This extraction step is usual in the field of plant extracts, and a person skilled in the art is able to adjust the reaction parameters, on the basis of his general knowledge.

At the end of this extraction step, an extract of flowers of Camellia Japonica Alba Plena is obtained, which can then, according to an advantageous aspect of the invention, be submitted to a decolorizing step, notably by means of activated charcoal in the presence of a solvent. The weight of activated charcoal is preferably between 0.5 and 50% of the weight of extract. It is notably possible to use one or more solvents selected from water, $C_1$-$C_4$ monohydric alcohols such as methanol, ethanol or isopropanol, polar organic solvents such as propylene glycol or dipropylene glycol, or any other solvent usually employed in this field. The volatile solvents can then be removed at reduced pressure.

The extract of flowers of Camellia Japonica Alba Plena obtained as described above can then be diluted in a suitable cosmetic solvent, notably in a monohydric alcohol, a glycol or glycerol, optionally mixed with water, before being used according to the invention at a rate of 0.00001 to 10 wt. %, preferably at a rate of 0.0001 to 5 wt. %, more preferably at a rate of 0.001 to 1 wt. %, and even more preferably at a rate of 0.05 to 0.1 wt. %, relative to the total weight of the composition.

The extract of flowers of Camellia Japonica Alba Plena is used according to the invention for cosmetic purposes, for moisturizing human skin or protecting it against drying. It can also be used for combating the cutaneous signs resulting from disturbance of the barrier function, including rough skin, discomfort including redness, tightness, tingling and itching, loss of radiance or sallow complexion, loss of suppleness of the skin and chapping.

The hydration effect of the composition used according to the invention can notably be measured by corneometry, according to the usual techniques that are well known by a person skilled in the art.

Preferably, the composition according to the invention, containing the extract of flowers of Camellia Japonica Alba Plena, is applied on skin that is dry, and preferably nonpathological. It can be applied advantageously on the skin of the face, of the neck and optionally of the cleavage or, as a variant, on any part of the body.

The composition containing this extract can be applied in the morning and/or in the evening, on all of the face, the neck and optionally the cleavage or even the body.

The composition used according to the invention generally comprises, in addition to the extract already described, a medium that is physiologically acceptable and preferably cosmetically acceptable, i.e. which is suitable for use in contact with human skin without risk of toxicity, of incompatibility, of instability, of allergic response and notably that does not cause sensations of discomfort (redness, tightness, tingling etc.) that are unacceptable for the user.

This medium generally contains water and optionally other solvents such as ethanol.

The composition used according to the invention can be in any form suitable for topical application on the skin and in particular in the form of oil-in-water, water-in-oil or multiple (W/O/W or O/W/O) emulsion, which can optionally be microemulsions or nanoemulsions, or in the form of aqueous dispersion, solution, aqueous gel or powder. It is preferable for this composition to be in the form of an oil-in-water emulsion.

This composition is preferably used as a product for care or for cleaning of the skin of the face and/or of the body and it can notably be in the form of fluid, gel or mousse, packaged for example in a pump-action spray bottle, an aerosol or a tube, or as cream packaged for example in a pot. As a variant, it can have the form of a makeup product and in particular a foundation or a loose or compacted powder.

Apart from the extract of flowers of Camellia Japonica Alba Plena described above, the composition according to the invention can also comprise at least one additive that is usual in the cosmetic field, for example at least one compound selected from a gelling agent and/or thickener, a surfactant or co-surfactant, a liquid fat or an oil, a wax, a silicone elastomer, a sun filter, a dye, a matting agent or a filler, a pigment, a lifting agent, a preservative, a sequestering agent, a perfume and mixtures thereof.

Notably, the composition according to the invention can contain, nonexhaustively, one or more of the following additives:
  One or more agents for gelling and/or thickening the aqueous phase, selected for example from the crosslinked or noncrosslinked, hydrophilic or amphiphilic homo- and copolymers, of acryloylmethylpropane sulfonic acid (AMPS) and/or of acrylamide and/or acrylic acid and/or salts or esters of acrylic acid such as ammonium acryloyldimethyltaurate/VP copolymer and ammonium acryloyldimethyl-taurate/beheneth-25 methacrylate copolymer, notably those sold under the names Aristoflex® AVC and HMB from Clariant, or acrylates/C10-30 Alkyl Acrylate Crosspolymer sold under the trade name PEMULEN® TR-1 or TR-2, Carbopol® 1382, Carbopol® Ultrez 20 by the company Novéon, cellulosic derivatives, gums of vegetable origin (acacia gum or gum arabic, agar, guar, carob, alginates, carrageenans, pectin) or of microbial origin (xanthan, pullulan), clays (laponite). Said gelling and/or thickening agent can be present in the composition at a content of the order of 0.01 to 5 wt. %, relative to the total weight of the composition;

One or more surfactants, preferably emulsifiers, whether nonionic, anionic, cationic or amphoteric, and in particular the esters of fatty acids and of polyols such as alkoxylated (more particularly polyethoxylated) esters of fatty acids and of glycerol, alkoxylated esters of fatty acids and of sorbitan, alkoxylated (ethoxylated and/or propoxylated) esters of fatty acids such as the mixture PEG-100 Stearate/Glyceryl Stearate marketed for example by the company Croda Inc. under the name Arlacel® 165 and the esters of fatty acids and of sucrose such as sucrose stearate; ethers of fatty alcohol and of sugar, notably the alkylpolyglucosides (APG) such as decylglucoside and laurylglucoside marketed for example by the company Henkel under the respective names Plantaren® 2000 and Plantaren® 1200, cetearyl glucoside optionally mixed with cetearyl alcohol, marketed for example under the name Montanov® 68 by the company Seppic, as well as arachidyl glucoside, for example in the form of the mixture of arachidyl and behenyl alcohols and of arachidyl glucoside marketed under the name Montanov® 202 by the company Seppic; ethers of fatty alcohols and of polyethylene glycol; polysiloxane modified polyethers; betaine and its derivatives; polyquaterniums; ethoxylated sulfate salts of fatty alcohols; sulfosuccinates; sarcosinates; alkyl and dialkyl phosphates and their salts; and soaps of fatty acids. Said surfactant can be present in the composition at a content of the order from 0.1 to 8%, preferably 0.5 to 3 wt. %, relative to the total weight of the composition;

One or more co-surfactants such as the linear fatty alcohols with a long carbon chain (C14-C20) and in particular cetyl and stearyl alcohols, said surfactant being present in the composition at a rate from 0.1 to 5%, preferably 0.5 to 2 wt. %, relative to the total weight of the composition;

One or more fats that are liquid at room temperature, commonly called volatile or nonvolatile, hydrocarbon, silicone, linear, cyclic or branched oil(s), for example, silicone oils such as polydimethylsiloxanes (dimethicones), polyalkylcyclosiloxanes (cyclomethicones) and polyalkylphenylsiloxanes (phenyldimethicones); synthetic oils such as fluorinated oils, alkyl benzoates and branched hydrocarbons such as polyisobutylene, isododecane; mineral oils (paraffin); vegetable oils (sweet almond oil, macadamia oil, blackcurrant seed oil, jojoba oil or *camelina sativa* oil such as the oil sold under the trade name Lipex® Omega 3/6 by the company Unipex); fatty alcohols, fatty amides, fatty acids or esters such as the benzoate of C12-C15 alcohols sold under the trade name Finsolv® TN by the company Innospec or isononyl isononanoate sold under the trade name Wickenol® 151 by the company Alzo Inc., octyl palmitate, isopropyl lanolate, the triglycerides including those of capric/caprylic acids, dicaprylyl carbonate sold under the name Cetiol® CC by the company Cognis; preferably at a rate from 0.1 to about 10%, preferably from 0.5 to 5 wt. %, relative to the total weight of the composition;

One or more waxes (compounds that are solid or substantially solid at room temperature, and whose melting point is generally above 35° C.), such as ozokerite, polyethylene wax, beeswax or carnauba wax, preferably at a rate from 0.01 to about 5%, preferably 0.5 to 5 wt. %, relative to the total weight of the composition;

One or more silicone elastomers notably obtained by reaction, in the presence of a catalyst, of a polysiloxane having at least one reactive group (notably hydrogen or vinyl) and bearing at least one alkyl (notably methyl) or phenyl end and/or side group, with an organosilicone such as an organohydrogen polysiloxane, preferably at a rate from 0.1 to about 20%, preferably 0.25 to 15 wt. %, relative to the total weight of the composition;

One or more sun filters, notably organic filters, such as derivatives of dibenzoylmethane (including butyl methoxydibenzoylmethane sold in particular by DSM under the trade name Parsol® 1789), derivatives of cinnamic acid (including ethylhexyl methoxycinnamate sold in particular by DSM under the trade name Parsol® MCX), salicylates, para-aminobenzoic acids, β-β'-diphenylacrylates, benzophenones, derivatives of benzylidene camphor, phenylbenzimidazoles, triazines, phenylbenzotriazoles and anthranilic derivatives; or inorganic filters, based on mineral oxides in the form of pigments or nanopigments, coated or uncoated, and in particular based on titanium dioxide or zinc oxide; preferably at a rate from 0.1 to about 30%, more preferably from 0.5 to 20 wt. %, relative to the total weight of the composition;

One or more water-soluble dyes such as, for example, disodium salt of ponceau, disodium salt of alizarin green, quinoline yellow, trisodium salt of amaranth, disodium salt of tartrazine, monosodium salt of rhodamine, disodium salt of fuchsin or xanthophyll, preferably at a rate from 0.1 to about 2 wt. %, relative to the total weight of the composition;

One or more fillers, in particular of matting agents or fillers with hazing effect, and in particular powders with soft-focus effect.

"Filler" means particles that are colorless or white, mineral or synthetic, lamellar or nonlamellar, suitable for giving the composition body or stiffness and/or softness, a matt look and immediate uniformity on application. These fillers can notably modify or even mask wrinkles by a camouflage effect, or a blurring effect.

The matting agents can be selected from matting polymers (in solution, in dispersion or in the form of particles) and inorganic particles that reduce the shininess of the skin and make the complexion more even.

The matting agent can notably be selected from starch, talc, cellulose microbeads, vegetable fibres, synthetic fibres, in particular polyamides (powders of Nylon® such as Nylon-12 (Orgasol® marketed by the company Atochem), microspheres of acrylic copolymers notably of polymethyl methacrylate (PMMA particles or the Micropearl® M310 particles sold by the company Seppic), silica powders, silicone resin powders, acrylic polymer powders, polyethylene powders, crosslinked elastomeric organopolysiloxanes (notably marketed under the names KSG® by the company Shin-Etsu, under the names Trefil®, BY29® or EPSX® by the company Dow Corning or under the names Gransil® by the company Grant Industries), composite powders of talc/titanium dioxide/alumina/silica, silicate powders, and mixtures thereof.

The fillers with "soft focus" effect can give transparency to the complexion and a blurred effect. Preferably, the "soft focus" fillers have an average particle size less than or equal to 30 microns, more preferably less than or equal to 15 microns. These "soft focus" fillers can be of any shape and in particular can be spherical or nonspherical. They can be selected from powders of silica and silicates, notably of alumina, powders of the polymethyl methacrylate type (PMMA or Micropearl® M310), talc, silica/TiO$_2$ or silica/zinc oxide composites, polyethylene powders, starch powders, polyamide powders, powders of styrene/acrylic copolymers, silicone elastomers, and mixtures thereof.

Preferably these matting agents or fillers with soft-focus effect are used at a rate from 0.1 to about 10 wt. %, relative to the total weight of the composition, preferably at a rate from 0.1 to about 7 wt. %.

One or more pigments—white or colored, nacreous or not, mineral and/or organic, coated or uncoated, insoluble in the medium, intended for coloring and/or opacifying the composition. They can be of the usual size or nanometric. We may mention, among the mineral pigments, titanium dioxide, optionally surface-treated, oxides of iron or of chromium, manganese violet, ultramarine blue, chromium hydroxide and ferric blue. Among organic pigments, we may mention carbon black, pigments of the D&C type, and lakes based on carmine, barium, strontium, calcium, aluminum. The nacreous pigments or nacres are iridescent particles which reflect the light. These nacreous pigments can be selected from white nacreous pigments such as mica covered with titanium, or bismuth oxychloride, colored nacreous pigments such as titanium mica with iron oxides. The pigments can have undergone a surface treatment. Preferably, these pigments are used at a rate from 0.1 to about 10 wt. %, relative to the total weight of the composition, preferably at a rate from 0.1 to about 5 wt. %.

One or more lifting agents. "Lifting agent" means a compound suitable for stretching the skin and, by this stretching effect, smoothing the skin and causing an immediate reduction or even disappearance of wrinkles and lines. As lifting agents, we may mention polymers of natural origin; mixed silicates; colloidal particles of inorganic fillers; synthetic polymers; and mixtures thereof. We may mention notably: polymers of vegetable or microbial origin, polymers derived from integumentary appendages, egg proteins and latices of natural origin. These polymers are preferably hydrophilic. As polymers of vegetable origin, we may mention in particular proteins and hydrolyzates of proteins, and more particularly extracts of cereals, of leguminous plants and oleaginous plants, such as extracts of maize, of rye, of wheat, of buckwheat, of sesame, of spelt, of pea, of tapioca, of bean, of lentil, of soya and of lupine. Other lifting agents that can be used according to the invention are polysaccharides of natural origin, notably starch obtained notably from rice, maize, tapioca, potato, manioc, pea; carrageenans, acacia gums (gum arabic), alginates, agars, gellans, xanthan gums, cellulosic polymers and pectins, advantageously in aqueous dispersion of microparticles of gel, cellulose derivatives, and mixtures thereof. The synthetic polymers are generally in the form of a latex or of a pseudolatex and can be of the polycondensate type or can be obtained by radical polymerization. We may mention notably dispersions of polyester/polyurethane and of polyether/polyurethane. Preferably, the lifting agent is a copolymer of PVP/dimethiconylacrylate and of hydrophilic polyurethane (Aquamere® S-2011®) from the company Hydromer).

One or more preservative(s);
sequestering agents such as salts of EDTA;
perfumes;
and mixtures thereof.

Examples of such additives are notably mentioned in the CTFA Dictionary (International Cosmetic Ingredient Dictionary and Handbook published by The Cosmetic, Toiletry and Fragrance Association, 11th Edition, 2006) which describes a wide variety, without limitation, of cosmetic and pharmaceutical ingredients usually employed in the skin care industry, which are suitable for use as additional ingredients in the compositions according to the present invention.

A person skilled in the art is capable of selecting, from all of these possible additives, both the composition and the amount of those to be added to the composition, in such a way that the latter retains all of its properties.

Moreover, the composition according to the present invention can optionally contain various active agents, which can be selected from the group comprising vitamins, antioxidants, hydrating agents, antipollution agents, keratolytic agents, astringents, antiinflammatories, bleaching agents and agents promoting the microcirculation.

Examples of vitamins include vitamins A, B1, B2, B6, C and E and their derivatives, pantothenic acid and its derivatives and biotin.

Examples of antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopherol acetate, tocopherol sorbate and other esters of tocopherol; BHT and BHA; esters of gallic acid, phosphoric acid, citric acid, maleic acid, malonic acid, succinic acid, fumaric acid, cephalin, hexametaphosphate, phytic acid, and plant extracts, for example from roots of *Zingiber officinale* (ginger) such as Blue Malagasy Ginger marketed by the company BIOLANDES, from *Chondrus crispus, Rhodiola, Thermus thermophilus*, the leaf of mate, oak wood, bark of Rapet Kayu, the leaves of Sakura and the leaves of ylang ylang.

Examples of hydrating agents include polyethylene glycol, propylene glycol, dipropylene glycol, glycerol, butylene glycol, xylitol, sorbitol, maltitol, mucopolysaccharides, such as chondroitin sulfuric acid, hyaluronic acid of high or of low molecular weight or hyaluronic acid potentiated by a silanol derivative such as the active substance Epidermosil® marketed by the company Exymol, and mucoitinsulfuric acid; caronic acid; atelocollagen; chloresteryl-12-hydroxystearate; biliary salts, a principal component of NHF (natural hydration factor) such as a salt of pyrrolidone carboxylic acid and a salt of lactic acid, an amino acid analog such as urea, cysteine and serine; a short-chain soluble collagen, diglycerol PPGs, homo- and copolymers of 2-methacryloyloxyethylphosphorylcholine such as Lipidure HM and Lipidure PBM from NOF; allantoin; glycerol derivatives such as PEG/PPG/polybutylene glycol-8/5/3 glycerol from NOF sold under the trade name Wilbride® S753 or glyceryl-polymethacrylate from Sederma sold under the trade name Lubragel® MS; trimethylglycine sold under the trade name Aminocoat® by the company Asahi Kasei Chemicals and various plant extracts such as extracts of *Castanea sativa*, hydrolyzed hazelnut proteins, polysaccharides of *Tuberosa polyanthes*, oil from the stone of *Argania spinosa* and extracts of nacre containing a conchyoline, which are sold notably by the company Maruzen (Japan) under the trade name Pearl Extract®.

Other examples of hydrating agents include compounds stimulating expression of matriptase MT/SP1, such as an extract of carob pulp, as well as agents that stimulate the expression of CERT, of ARNT2 or of FN3K or FN3K RP; agents that increase the proliferation or differentiation of keratinocytes, either directly, or indirectly by stimulating for example the production of β-endorphins, such as extracts of *Thermus thermophilus* or of husks of beans of *Theobroma cacao*, water-soluble extracts of maize, peptide extracts of *Voandzeia subterranea* and niacinamide; epidermal lipids and agents that increase the synthesis of epidermal lipids, either directly, or by stimulating certain β-glucosidases that modulate deglycosylation of lipid precursors such as glucosylceramide to ceramides, such as phospholipids, ceramides, hydrolyzates of lupine protein and derivatives of dihydrojasmonic acid.

Examples of antipollution agents include extract of seeds of *Moringa pterygosperma* (for example Purisoft® from LSN); extract of karite butter (for example Detoxyl® from Silab), a mixture of extract of ivy, of phytic acid, of extract of sunflower seed (for example Osmopur® from Sederma).

Examples of keratolytic agents include α-hydroxy acids (for example glycolic, lactic, citric, malic, mandelic, or tartaric acids) and β-hydroxy acids (for example salicylic acid), and esters thereof, such as C12-13 alkyl lactates, and plant extracts containing these hydroxy acids, such as extracts of *Hibiscus sabdriffa*.

Examples of astringents include extracts of hamamelis.

Examples of antiinflammatory agents include bisabolol, allantoin, tranexamic acid, zinc oxide, sulfur oxide and its derivatives, chondroitin sulfate, glycyrrhizinic acid and its derivatives such as glycyrrhizinates.

Examples of bleaching agents include arbutin and its derivatives, ferulic acid (such as Cytovector®: water, glycol, lecithin, ferulic acid, hydroxyethylcellulose, marketed by BASF) and its derivatives, kojic acid, resorcinol, lipoic acid and its derivatives such as the monolipoate of resveratrol diacetate as described in patent application WO2006134282, ellagic acid, leucodopachrome and its derivatives, vitamin B3, linoleic acid and its derivatives, ceramides and their homologs, a peptide such as described in patent application WO2009010356, a bioprecursor as described in patent application WO2006134282 or a tranexamate salt such as hydrochloride salt of cetyl tranexamate, an extract of liquorice (extract of *Glycyrrhiza glabra*), which is notably sold by the company Maruzen under the trade name Licorice Extract®, a bleaching agent also having an antioxidant effect, such as the compounds of vitamin C, including the ascorbate salts, ascorbyl esters of fatty acids or of sorbic acid, and other derivatives of ascorbic acid, for example, ascorbyl phosphates, such as magnesium ascorbyl phosphate and sodium ascorbyl phosphate, or saccharide esters of ascorbic acid, which include, for example, ascorbyl-2-glucoside, L-ascorbate of 2-O-alpha-D-glucopyranosyl, or L-ascorbate of 6-O-beta-D-galactopyranosyl. An active agent of this type is sold in particular by the company DKSH under the trade name Ascorbyl Glucoside®.

Examples of agents promoting the microcirculation include an extract of lupine (such as Eclaline® from Silab), of ruscus, of horse chestnut, of ivy, of ginseng or of melilot, caffeine, nicotinate and its derivatives, an extract of alga of *Corallina officinalis* such as that marketed by CODIF; and mixtures thereof. These agents that act on the microcirculation of the skin can be used to prevent dulling of the complexion and/or to improve uniformity and radiance.

The composition used according to the invention can moreover comprise, in addition to an extract of flowers of Camellia Japonica Alba Plena, at least one active substance selected from: agents that stimulate the expression of tensin 1 such as an extract of elemi; agents that stimulate the expression of FN3K and/or of FN3K RP such as an extract of *Butea frondosa*; agents that stimulate the expression of CERT or of ARNT2; agents that stimulate the production of growth factors; antiglycation agents or deglycants; agents that increase the synthesis of collagen or prevent its degradation (anti-collagenase agents, notably inhibitors of matrix metalloproteinases), in particular agents that increase the synthesis of collagen IV and/or of hyaluronan and/or of fibronectin, such as at least one acylated oligopeptide, notably that marketed by the company SEDERMA under the trade name Matrixyl® 3000; agents that increase the synthesis of elastin or prevent its degradation (anti-elastase agents); agents that increase the synthesis of glycosaminoglycans or of proteoglycans or prevent their degradation (anti-proteoglycanase agents) such as the active substance Epidermosil® (hyaluronic acid combined with methylsilanetriol) marketed by the company Exsymol; agents that stimulate the synthesis of integrins by fibroblasts; agents that increase the proliferation of fibroblasts; agents facilitating percutaneous absorption such as alcohols, fatty alcohols and fatty acids and their ester or ether derivatives, pyrrolidones, 4-alkyl-oxazolidin-2-ones such as 4-decyloxazolidin-2-one; terpenes, essential oils and α-hydroxy acids; and mixtures thereof, without this list being exhaustive.

It became clear to the applicant that a combination of at least one extract of flowers of Camellia Japonica Alba Plena with one or more of the active ingredients described above made it possible to combine, advantageously in one and the same formula, the effects of these combinations of active substances and thus obtain maximum, long-lasting hydration of the skin as well as improve radiance and/or evenness of complexion and decrease the appearance of an off-color complexion.

The cosmetic composition according to the invention therefore contains advantageously at least one extract of flowers of Camellia Japonica Alba Plena and at least one active substance selected from: hydrating agents, antioxidants, agents promoting the microcirculation, and mixtures thereof.

More particularly, it can contain at least one active substance selected from: a fermented extract of *Thermus thermophilus*; an extract of root of *Zingiber officinale* (ginger); hyaluronic acid and its derivatives; an extract of carob pulp; and mixtures thereof.

The invention will now be illustrated by the following nonlimiting examples.

EXAMPLES

Example 1

Preparation of an Extract of Camellia Japonica Alba Plena

1) Alcoholic Extraction

Put 35 kg of flowers of Camellia Japonica Alba Plena in a 500-liter stainless steel reactor.

Add 215 l of 96% ethanol (volume/volume).

Heat the reactor to 65° C. and keep it at this temperature for 6 hours.

Then filter the material in order to remove the flowers of Camellia Japonica Alba Plena.

Collect the filtrate.

Then evaporate the solvent in a rotary evaporator under vacuum.

This gives 1.78 kg of extract of flowers of Japonica Alba Plena.

The yield in this operation is 5.1%.

2) Decolorizing of the Extract

Wash the extract with hot 96% ethanol (volume/volume) and activated charcoal. For this, mix 1.78 kg of extract with 14 l of 96% ethanol and 1.75 kg of activated charcoal.

Stir vigorously for 2 hours at room temperature then leave to stand for 2 hours. After filtration of the solution on a Büchner, the primary filtrate is recovered.

Filter this filtrate again on a conical filter to remove the last residues of activated charcoal, then evaporate the ethanol in a rotary evaporator under vacuum.

The total yield of the process is 3.5%.

Before being tested on the cells of the skin as described in examples 2 to 5 below, the extract is diluted to 25% in glycerol.

Example 2

Test of Stimulation of Expression of mRNA of HSP32 (RT-PCR) on Keratinocytes Treated with an Extract of Flowers of Camellia Japonica Alba Plena Protocol:

The effect of the extract from Example 1 was evaluated by RT-PCR (real-time polymerase chain reaction), in order to quantify the expression of messenger RNA of HSP32 in a treated sample relative to an untreated sample. The results are normalized relative to the expression of domestic genes in these samples.

The results are expressed as the factor of increase or decrease of expression of the target gene (HSP32) in the treated sample.

The cDNA/mRNA sequences of the genes investigated were obtained according to the work of Jonak C. et al. (2005, Hum. Patol)

Target gene: HSP32 (HO-1)

Domestic gene: GAPDH

The mRNA was isolated using the Qiagen RNeasy kit (QIAGEN) according to the manufacturer's recommendations. Reverse transcription to cDNA was carried out by means of the kit gene Amp RNA PCR (Applied Biosystems) according to the manufacturer's recommendations.

Keratinocytes derived from neonatal foreskins (Cascade Biologics, Invitrogen, CA) were seeded in 6-well plates and cultivated in growing medium for keratinocytes (Epilife®+ EDGS, Cascade Biologics, Invitrogen, CA). After 24 h of culture in a stove at 37° C., the confluent cells were washed with PBS buffer (Invitrogen, CA) and incubated with basic specific medium (Epilife®, Cascade Biologics, Invitrogen, CA) containing the test extract, for 24 h. After investigating the cytotoxicity of the extract, its activity was evaluated.

Measurement by real-time PCR was carried out using the apparatus iCYCLER IQ (Biorad) with SYBR Green I detection. In all the tests, the cDNA was amplified using a standardized program. Each sample was loaded with Supermixe IQ SYBR Green I, water and primer (stock); the final amount of cDNA per reaction corresponded to 75 ng of total RNA used for reverse transcription.

Relative quantification of the expression of the target gene was performed using Pfaffl's mathematical model (Pfaffl, M W, Nucleic Acids Res. 29(9), p. E45, 2001).

The test was performed on normal human keratinocytes cultured in triplicate. The results obtained were confirmed using cells from three different donors.

Results:

TABLE 1

|  | Concentration[1] | Stimulation of mRNA of HSP32 | Standard deviation |
| --- | --- | --- | --- |
| Untreated keratinocytes | — | 1.0 | 0.1 |
| Extract of flowers of *Camellia Japonica* Alba Plena according to example 1 | 0.05% | 2.8 | 0.5 |

[1]the concentrations of the extracts are expressed as weight of raw extract per weight of preparation (the extract obtained according to example 1 being diluted in the growing medium for keratinocytes)

The extract of flowers of Camellia Japonica Alba Plena tested at 0.05% stimulates the expression of mRNA of HSP32 by a factor of 2.8, relative to the untreated control.

Example 3

Test of Stimulation of Expression of the HSP27 Protein on Keratinocytes Treated with Various Extracts of Flowers of Camellia Japonica Protocol:

Stimulation of expression of the HSP27 protein was investigated with various extracts of Camellia flower, i.e. the extract obtained according to Example 1 and extracts of flowers of *Camellia japonica* Dr Tinsley, *Camellia japonica* Broceliande and *Camellia japonica* Fire Falls, all obtained according to an extraction process identical as that described in Example 1. The experiments were performed on a culture of keratinocytes cultured in identical conditions to those described in example 2.

The test was performed on normal human keratinocytes cultured in triplicate and treated for 24 h. The results obtained were confirmed using cells from two different donors.

Quantitative evaluation of the concentrations of HSP27 in the cell cultures was carried out by the ELISA method using the immunological kit test DuoSet_IC® (DYC1580-2, R&D Systems, Minn., USA) and following the protocol described by the manufacturer. The lysed cells were placed on 96-well microtitration plates. They were then treated with a solution of biotinylated anti-HSP27 monoclonal antibody. After incubation overnight at 4° C., the plate was rinsed several times and then incubated in the presence of the test samples and the other reagents described in the protocol. Detection was carried out at 450/540 nm (Steptavidin-HRP format) using a microplate reader and the results were calculated using four logistic parameters of the curve (4-PL).

Results:

TABLE 2

|  | Concentration[1] | Stimulation of expression of HSP27(%) | Standard deviation |
| --- | --- | --- | --- |
| Untreated keratinocytes | — | 100 | 0 |

TABLE 2-continued

|  | Concentration[1] | Stimulation of expression of HSP27(%) | Standard deviation |
|---|---|---|---|
| Extract of flowers of Camellia Japonica Alba Plena according to example 1 | 0.0125% | 219.3 | 24.3 |
|  | 0.025% | 283.7 | 44.5 |
| Extract of flowers of Camellia japonica Dr Tinsley | 0.0125% | 177.4 | 0.4 |
|  | 0.025% | 181.4 | 6.8 |
| Extract of flowers of Camellia japonica Broceliande | 0.0125% | 151.9 | 14.2 |
|  | 0.025% | 168.1 | 14.0 |
| Extract of flowers of Camellia japonica Fire Falls | 0.0125% | 161.3 | 23.9 |
|  | 0.025% | 184.0 | 20.8 |

[1]the concentrations of the extracts are expressed as weight of raw extract per weight of preparation (the extract obtained according to example 1 being diluted in the growing medium for keratinocytes)

The extract of flowers of Camellia Japonica Alba Plena tested significantly stimulates the expression of mRNA of HSP27 relative to the untreated control, and this stimulation is higher than for other extracts of Camellia japonica at the concentrations tested.

Example 4

Test of Stimulation of Expression of Protein PPAR-β/δ on Keratinocytes Treated with Various Extracts of Flowers of Camellia Japonica Protocol:

Stimulation of expression of the protein PPAR-β/δ was investigated with various extracts of Camellia flower, i.e. the extract obtained according to Example 1 and extracts of flowers of *Camellia japonica* Dr Tinsley, *Camellia japonica Broceliande* and *Camellia japonica* Fire Falls, all obtained according to an extraction process identical as that described in Example 1. The experiments were performed on a culture of keratinocytes cultured in conditions identical to those described in example 2.

The test was performed on normal human keratinocytes cultured in triplicate. The results obtained were confirmed using cells from two different donors, except for Camellia Fire Falls were the cells from 3 donors were used.

Quantitative evaluation of the concentrations of PPAR-β/δ in the cell cultures was performed by conventional methods, such as immuno-enzyme assay or more particularly a Western Blot analysis.

The PPAR-β/δ proteins are separated by electrophoresis on 4-12% gel SDS-PAGE (Invitrogen, CA, USA) after quantification with the micro-BCA protein quantification kit (Pierce, N.Y., USA). After transfer onto PVDF membrane (GE Healthcare, NJ, USA) according to a standard protocol, the PPAR-β/δ proteins are incubated with the anti-PPAR-β/δ primary antibody (Cayman, Mich., USA) overnight at 4° C. Then the second incubation takes place with the secondary antibody (Goat anti-rabbit IgG-HRP conjugate; GE Healthcare) directed against the primary antibody generally for 1 hour at room temperature. The presence of PPAR-β/δ on the membrane is detected by immunodetection by means of a chemiluminescence detection kit following the manufacturer's instructions (Pierce, N.Y., USA). The bands are quantified by means of the AlphaInnotech imager (San Leandro, Calif., USA).

Results:

TABLE 3

|  | Concentration[1] | Stimulation of PPAR-β/δ (%) | Standard deviation |
|---|---|---|---|
| Untreated keratinocytes | — | 100 | 0 |
| Extract of flowers of Camellia Japonica Alba Plena according to example 1 | 0.00625% | 161.2 | 8.8 |
|  | 0.0125% | 203.1 | 30.6 |
|  | 0.05% | 155.7 | 16.1 |
| Extract of flowers of Camellia japonica Dr Tinsley | 0.00625% | 93.8 | 4.0 |
|  | 0.0125% | 98.3 | 2.1 |
|  | 0.05% | 80.0 | 26.9 |
| Extract of flowers of Camellia japonica Broceliande | 0.00625% | 81.6 | 1.8 |
|  | 0.0125% | 87.3 | 1.1 |
|  | 0.05% | 99.0 | 9.7 |
| Extract of flowers of Camellia japonica Fire Falls | 0.00625% | 118.2 | 2.5 |
|  | 0.0125% | 122.2 | 20.3 |
|  | 0.05% | 90.3 | 9.0 |

[1]the concentrations of the extracts are expressed as weight of raw extract per weight of preparation (the extract obtained according to example 1 being diluted in the growing medium for keratinocytes)

The extract of flowers of Camellia Japonica Alba Plena tested significantly stimulates the expression of PPAR-β/δ, relative to the untreated control and this stimulation is far higher than for other extracts of *Camellia japonica* at the concentrations tested.

Example 5

Cosmetic Composition (Serum O/W)

The following composition can be prepared conventionally by a person skilled in the art. The quantities given below are expressed in percentages by weight. The ingredients in upper case are identified according to INCI name.

| INCI Name | % (weight/weight) |
|---|---|
| WATER | Q.S. 100.00 |
| Chelating agent | 0.05 |
| pH adjuster | 0.05 |
| Preservative | 0.05 |
| Glycol | 3.25 |
| AMMONIUM ACRYLOYLDIMETHYLTAURATE/ VP COPOLYMER | 1.20 |
| ACRYLATES/C10-30 ALKYL ACRYLATE CROSSPOLYMER | 0.20 |
| GLYCERIN | 3.00 |
| GLYCERYLPOLYMETHACRYLATE | 4.18 |
| SODIUM ACETYLATED HYALURONATE | 0.05 |
| PEG/PPG/POLYBUTYLENE GLYCOL-8/5/3 GLYCERIN | 2.00 |
| SODIUM PCA | 3.00 |
| Oil | 10.00 |
| ALCOHOL | 8.00 |
| FRAGRANCE | 0.30 |
| ZINGIBER OFFICINALE (GINGER) ROOT EXTRACT[1] | 0.10 |
| HYALURONIC ACID & SILANETRIOL & CITRIC ACID[2] | 5.00 |
| CAMELLIA JAPONICA FLOWER EXTRACT[3] | 0.05 |
| CROSSLINKED POLYMETHYLMETHACRYLATE[4] | 0.75 |
| HDI/TRIMETHYLOL HEXYLLACTONE CROSSPOLYMER & SILICA[5] | 0.75 |

-continued

| INCI Name | % (weight/weight) |
|---|---|
| AQUA (WATER) & *THERMUS THERMOPHILLUS* FERMENT & GLYCERIN & BIOTIN[5] | 3.00 |
| Extract of carob pulp | 0.10 |

[1] Blue Malagasy Ginger ® sold by the company BIOLANDES
[2] EPIDERMOSIL ® sold by the company EXSYMOL
[3] as described in Example 1
[4] MICROPEARL ® M310 from SEPPIC
[5] PLASTIC POWDER ® D-400/BPD-500 ® from KOBO
[6] VENUCEANE ® from SEDERMA This composition can be applied daily, morning and/or evening, on skin that is particularly dehydrated and/or exposed to aggressive factors of the environment, to improve comfort and make the complexion uniform.

The invention claimed is:

1. A cosmetic composition containing, in a physiologically acceptable medium, at least one extract of flowers of Camellia Japonica Alba Plena.

2. The composition according to claim 1, characterized in which the at least one extract additionally contains at least one active substance selected from: hydrating agents, antioxidants, or agents promoting the microcirculation, and mixtures thereof.

3. The composition according to claim 1, in which the at least one active substance is selected from: a fermented extract of *Thermus thermophilus*, an extract of root of *Zingiber officinale*, hyaluronic acid, or an extract of carob pulp, and mixtures thereof.

4. The composition according to claim 1, in which the at least one extract is obtained by alcoholic extraction with an extraction solvent comprising a monohydric alcohol and/or a glycol, optionally mixed with water.

5. The composition according to claim 4, in which the at least one extract additionally contains at least one active substance selected from: hydrating agents, antioxidants, agents promoting the microcirculation, and mixtures thereof.

6. The composition according to claim 4, in which the active substance is selected from: a fermented extract of *Thermus thermophilus*, an extract of root of *Zingiber officinale*, hyaluronic, an extract of carob pulp, and mixtures thereof.

7. The composition according to claim 4, in which the extraction solvent comprises a monohydric alcohol that is ethanol.

8. The composition according to claim 7, in which the at least one extract additionally contains at least one active substance selected from: hydrating agents, antioxidants, agents promoting the microcirculation, and mixtures thereof.

9. An extract of flowers of Camellia Japonica Alba Plena, the extract obtained by extraction of Camellia Japonica Alba Plena flowers with at least one alcoholic solvent.

10. The extract according to claim 9, in which the at least one extract is obtained by alcoholic extraction with an extraction solvent comprising a monohydric alcohol and/or a glycol, optionally mixed with water.

11. The extract according to claim 10, in which the extraction solvent comprises a monohydric alcohol that is ethanol.

12. A cosmetic process for moisturizing and/or protecting human skin against drying, comprising the application of the composition according to claim 1 on the skin.

13. The cosmetic process according to claim 12, characterized in that the composition is applied on dry, nonpathological skin.

* * * * *